(12) United States Patent
Yu et al.

(10) Patent No.: US 9,178,032 B2
(45) Date of Patent: Nov. 3, 2015

(54) GAS SENSOR AND MANUFACTURING METHOD THEREOF

(71) Applicant: Electronics and Telecommunications Research Institute, Daejeon (KR)

(72) Inventors: Young-Jun Yu, Daejeon (KR); Hongkyw Choi, Busan (KR); Jin Sik Choi, Daejeon (KR); Kwang Hyo Chung, Daejeon (KR); Jin Tae Kim, Daejeon (KR); Doo Hyeb Youn, Daejeon (KR); Choon Gi Choi, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 14/163,577

(22) Filed: Jan. 24, 2014

(65) Prior Publication Data

US 2014/0231933 A1    Aug. 21, 2014

(30) Foreign Application Priority Data

Feb. 15, 2013 (KR) .................. 10-2013-0016535
Aug. 27, 2013 (KR) .................. 10-2013-0101957

(51) Int. Cl.
*G01N 27/414* (2006.01)
*H01L 29/66* (2006.01)
*G01N 27/12* (2006.01)

(52) U.S. Cl.
CPC .............. *H01L 29/66* (2013.01); *G01N 27/128* (2013.01)

(58) Field of Classification Search
CPC .. G01N 27/4141; G01N 27/128; H01L 29/66; H01L 41/1132
USPC ............................... 438/24, 48; 257/252, 414
See application file for complete search history.

(56) References Cited

U.S. PATENT DOCUMENTS

| | | | |
|---|---|---|---|
| 6,433,356 B1 * | 8/2002 | Cahen et al. | 257/40 |
| 7,592,679 B1 * | 9/2009 | Kamins et al. | 257/414 |
| 8,176,767 B2 * | 5/2012 | Schneider et al. | 73/23.32 |
| 2005/0116831 A1 * | 6/2005 | Zribi | 340/632 |
| 2005/0139993 A1 * | 6/2005 | Lee et al. | 257/706 |
| 2007/0045756 A1 * | 3/2007 | Chang et al. | 257/414 |
| 2007/0114621 A1 * | 5/2007 | Wisnudel et al. | 257/414 |
| 2008/0064086 A1 * | 3/2008 | Lee et al. | 435/289.1 |
| 2009/0218220 A1 * | 9/2009 | Matter et al. | 204/424 |
| 2009/0221130 A1 * | 9/2009 | Asano | 438/478 |
| 2009/0312954 A1 * | 12/2009 | Utriainen | 702/23 |
| 2010/0161242 A1 * | 6/2010 | Wang et al. | 702/24 |

(Continued)

OTHER PUBLICATIONS

Rao, Fubo, et al. "Molecular nanosensors based on the inter-sheet tunneling effect of a bilayer graphene." Nano/Molecular Medicine and Engineering (NANOMED), 2010 IEEE 4th International Conference on. IEEE, 2010.*

(Continued)

*Primary Examiner* — Jarrett Stark
*Assistant Examiner* — Bitew Dinke
(74) *Attorney, Agent, or Firm* — Rabin & Berdo, P.C.

(57) ABSTRACT

Provided is a gas sensor including a substrate, a sensing electrode extended in a first direction on the substrate, and a plurality of heaters disposed in a second direction crossing the first direction on the substrate. The plurality of heaters is separated at both sides of the sensing electrode. The plurality of heaters includes graphene.

20 Claims, 10 Drawing Sheets

(56) References Cited

U.S. PATENT DOCUMENTS

| | | | |
|---|---|---|---|
| 2010/0264900 A1* | 10/2010 | Blackburn et al. | 324/71.1 |
| 2011/0068290 A1* | 3/2011 | Haddon et al. | 252/62.51 R |
| 2011/0068372 A1* | 3/2011 | Ren et al. | 257/194 |
| 2011/0101365 A1* | 5/2011 | Kim et al. | 257/66 |
| 2011/0120866 A1* | 5/2011 | Lee et al. | 204/431 |
| 2011/0138882 A1* | 6/2011 | Moon et al. | 73/31.06 |
| 2011/0227043 A1 | 9/2011 | Guo et al. | |
| 2012/0070910 A1* | 3/2012 | Ah et al. | 436/501 |
| 2012/0161106 A1* | 6/2012 | Kim et al. | 257/29 |
| 2012/0168724 A1* | 7/2012 | Park et al. | 257/29 |
| 2012/0198918 A1* | 8/2012 | Moon et al. | 73/31.06 |
| 2013/0018599 A1* | 1/2013 | Peng | 702/30 |
| 2013/0048950 A1* | 2/2013 | Levy et al. | 257/29 |
| 2013/0306934 A1* | 11/2013 | Lee | 257/12 |
| 2013/0307029 A1* | 11/2013 | Xu et al. | 257/253 |
| 2014/0070170 A1* | 3/2014 | Andersson et al. | 257/29 |
| 2014/0103298 A1* | 4/2014 | Lee et al. | 257/29 |
| 2014/0105790 A1* | 4/2014 | Gaudon et al. | 422/90 |
| 2014/0130779 A1* | 5/2014 | Fosaaen | 123/478 |
| 2014/0145148 A1* | 5/2014 | Lee | 257/29 |
| 2014/0193626 A1* | 7/2014 | Ozyilmaz et al. | 428/220 |
| 2014/0209983 A1* | 7/2014 | Burgi et al. | 257/253 |

OTHER PUBLICATIONS

Kang, Junmo, et al. "High-performance graphene-based transparent flexible heaters." Nano letters 11.12 (2011): 5154-5158.*

Jeong, Hu Young, et al. "Flexible room-temperature No. 2 gas sensors based on carbon nanotubes/reduced graphene hybrid films." Applied Physics Letters 96 (2010): 213105.*

Li, Weiwei, et al. "Reduced graphene oxide electrically contacted graphene sensor for highly sensitive nitric oxide detection." ACS nano 5.9 (2011): 6955-6961.*

Kochmann, Sven, Thomas Hirsch, and Otto S. Wolfbeis. "Graphenes in chemical sensors and biosensors." TrAC Trends in Analytical Chemistry 39 (2012): 87-113.*

Hu Young Jeong et al., "Flexible room-temperature No. 2 gas sensors based on carbon nanotubes/reduced grapheme hybrid films", Applied physics letters, vol. 96, pp. 213105, May 2010.

* cited by examiner

GAS SENSOR AND MANUFACTURING METHOD THEREOF

CROSS-REFERENCE TO RELATED APPLICATIONS

This U.S. non-provisional patent application claims priority under 35 U.S.C. §119 of Korean Patent Application Nos. 10-2013-0016535, filed on Feb. 15, 2013, and 10-2013-0101957, filed on Aug. 27, 2013, the entire contents of which are hereby incorporated by reference.

BACKGROUND

The present disclosure herein relates to a sensor and a manufacturing method thereof, and more particularly, to a gas sensor and a manufacturing method thereof.

Recently, according to the remarkable development in semiconductor industry, various microsensors and microheaters are under development. Since a semiconductor gas sensor has high sensitivity and low production unit cost, lots of applications thereof is expected. However, the thermal efficiency of the semiconductor gas sensor may be deteriorated. For example, the gas sensor needs a heater essentially. High power consumption restricts the application of the gas sensor. The reality is that the gas sensor is not practically applied in a field having restricted power supply such as a mobile device like a cellular phone, or a wireless sensor node. Thus, developments on a gas sensor including a high temperature heater of low power are actively conducted.

A general micro gas sensor may be a sliced portion micro gas sensor. The sliced portion micro gas sensor may include a heater layer on a substrate and a sensing layer on the heater layer. The heater layer may heat the sensing layer to activate. A common gas sensor includes a heater layer of a metal material and a sensing layer, and may be opaque. In addition, the heater layer of the metal material and the sensing layer may be weak to bending.

SUMMARY

The present disclosure provides a transparent gas sensor and a manufacturing method thereof.

The present disclosure also provides a flexible gas sensor and a manufacturing method thereof.

Embodiments of the inventive concept provide a gas sensor including a substrate, a sensing electrode extended in a first direction on the substrate, and a plurality of heaters disposed in a second direction crossing the first direction on the substrate. The plurality of heaters is separated at both sides of the sensing electrode. The plurality of heaters includes graphene.

In some embodiments, the sensing electrode may include the graphene or graphene oxide.

In other embodiments, the sensing electrode may include transition metal dichalcogenides.

In still other embodiments, the transition metal dichalcogenides may include molybdenum sulfide, tungsten sulfide, or niobium selenide.

In even other embodiments, the gas sensor may further include an interlayer insulating layer between the sensing electrode and the substrate, and a lower heater layer between the interlayer insulating layer and the substrate. The lower heater layer may include the graphene.

In yet other embodiments, the interlayer insulating layer may include a transparent dielectric material.

In further embodiments, the transparent dielectric material may include a silicon oxide layer, a silicon nitride layer, or a hexagonal boron nitride layer.

In still further embodiments, the gas sensor may further include a plurality of upper insulating patterns separated at both sides of the sensing electrode and extending in the second direction, and a plurality of upper heaters disposed on the plurality of upper insulating patterns. The upper heaters may include the graphene.

In even further embodiments, the upper insulating patterns may include a hexagonal boron nitride layer.

In yet further embodiments, the sensing electrode may include a first terminal, a channel connected to the first terminal and disposed between the heaters, and a second terminal connected to the channel and facing the first terminal. The upper insulating patterns and the upper heaters may be disposed on the channel.

In much further embodiments, the substrate may include a flexible substrate.

In still much further embodiments, the flexible substrate may be a transparent plastic substrate.

In other embodiments of the inventive concept, a manufacturing method of a gas sensor includes forming a sensing electrode in a first direction on a substrate, and forming a plurality of heaters in a second direction crossing the first direction at both sides of the sensing electrode. At least one of the sensing electrode and the heaters may include graphene.

In some embodiments, the manufacturing method may further include forming a lower heater layer between the sensing electrode and the substrate, and forming an interlayer insulating layer between the lower heater layer and the sensing layer.

In other embodiments, the manufacturing method may further include forming an upper insulating layer on the sensing electrode and the substrate, forming an upper heater layer on the upper insulating layer, and patterning the upper heater layer and the upper insulating layer to form upper insulating patterns and upper heaters at both side end portions of the sensing electrode in a first direction.

The gas sensor according to an embodiment of the inventive concept may include a substrate, a sensing electrode, and heaters. The substrate may include a flexible and transparent plastic substrate. The sensing electrode may be extended in a first direction on the substrate. The heaters may be separated from and disposed at both sides of the sensing electrode in a second direction crossing the first direction. The heaters may include graphene. The graphene may include carbon atoms of 6-membered ring. The graphene carbon atoms in a single layer are transparent. In addition, the carbon atoms have excellent elasticity and do not lose electrical properties even though being elongated or bent.

Therefore, the gas sensor according to an embodiment of the inventive concept may be transparent and flexible.

BRIEF DESCRIPTION OF THE DRAWINGS

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION OF THE EMBODIMENTS

Figure 1:
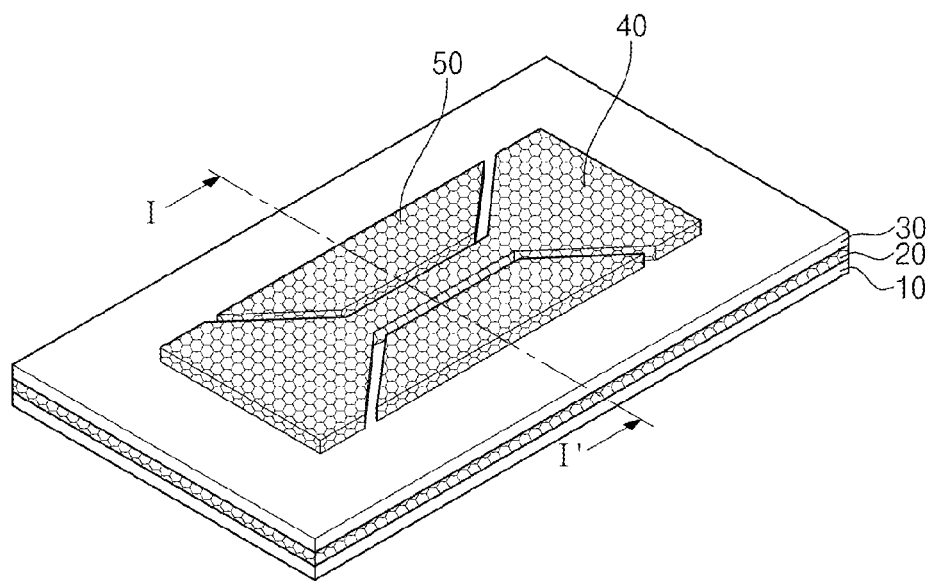
FIG. 1 is a perspective view of a gas sensor according to the first embodiment of the inventive concept.

Exemplary embodiments of the inventive concept will be described below in more detail with reference to the accompanying drawings. The inventive concept may, however, be embodied in different forms and should not be construed as limited to the embodiments set forth herein. Rather, these embodiments are provided so that this disclosure will be thorough and complete, and will fully convey the scope of the inventive concept to those skilled in the art.

In the drawings, description on elements having no relation to the inventive concept is omitted for the clarity of explanation, and like reference numerals refer to like elements throughout. In the drawings, the dimensions of layers and regions are exaggerated for clarity of illustration.

It will be further understood that the terms "comprises" and/or "comprising," when used in this specification, specify the presence of stated features, numerals, steps, operations, components, parts or combinations thereof, but do not preclude the presence or addition of one or more other features, numerals, steps, operations, components, parts or combinations thereof.

It will also be understood that when a layer (or film) is referred to as being 'on' another layer or substrate, it can be directly on the other layer or substrate, or intervening layers may also be present. In addition, it will also be understood that when a layer is referred to as being 'directly on' another layers, it can be on the other layer without an intervening layer.

Hereinafter, exemplary embodiments of the inventive concept will be described in detail with reference to the accompanying drawings.

Figure 2:
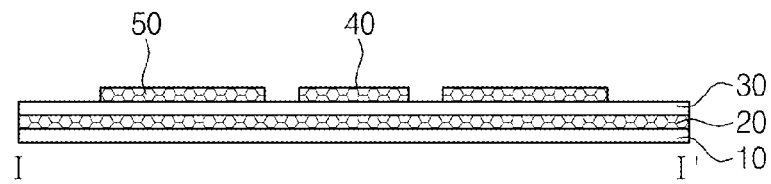
FIG. 2 is a cross-sectional view taken along line I-I' of FIG. 1.
Figure 3:
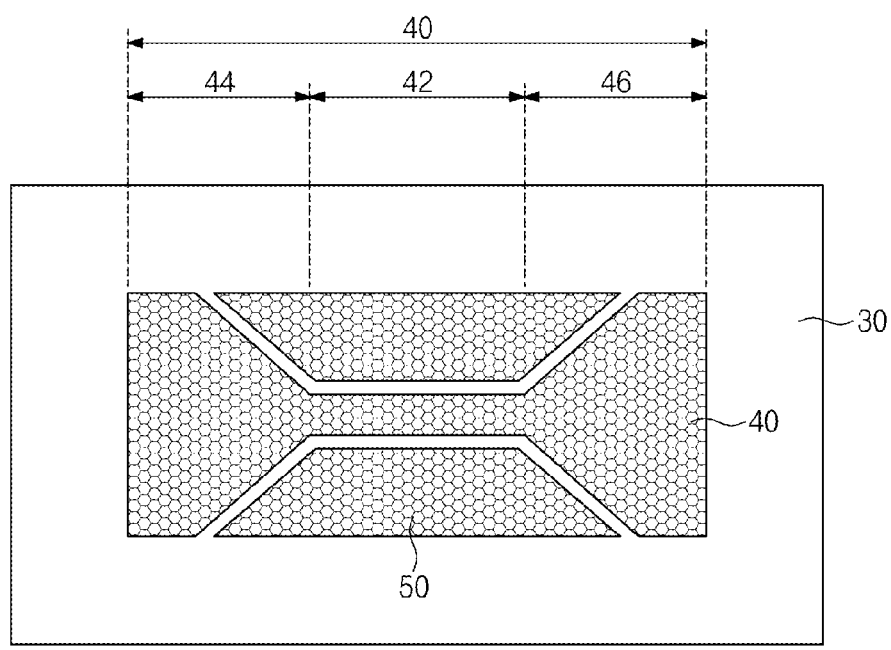
FIG. 3 is a plan view of FIG. 1.

FIG. 1 is a perspective view of a gas sensor according to the first embodiment of the inventive concept. FIG. 2 is a cross-sectional view taken along line I-I' of FIG. 1. FIG. 3 is a plan view of FIG. 1.

Referring to FIGS. 1 to 3, a gas sensor according to an embodiment of the inventive concept may include a substrate 10, a lower heater layer 20, an interlayer insulating layer 30, a sensing electrode 40, and heaters 50.

The substrate 10 may include a flexible substrate such as plastic. The flexible substrate may be transparent. The lower heater layer 20 may be disposed on the substrate 10. The lower heater layer 20 may include graphene. The graphene is a material constituting a thin and planar structure having a honeycomb shape through the interconnection between carbon atoms, and has electrical properties of emitting heat by an external power. The carbon atoms are interconnected and make one carbon atom layer. The graphene may be a single layer or a multi-layer of the carbon atoms. The graphene layer of the single layer may have the same thickness as that of one carbon atom. The carbon atoms have a 6-membered ring as a basic unit. Since the single layer has light absorbance of about 2% or less, the graphene may be transparent. In addition, the carbon atoms of the graphene have excellent elasticity, and do not lose electrical properties by elongation or bending. The graphene may be formed by means of a mechanical exfoliation method or a chemical vapor deposition method. According to the mechanical exfoliation method, an adhesive tape is attached to a graphite source to transfer the graphene to the substrate 10.

The interlayer insulating layer 30 may be disposed on the lower heater layer 20. The interlayer insulating layer 30 may include a transparent dielectric layer. The interlayer insulating layer 30 of the transparent dielectric layer may include a silicon oxide layer, a silicon nitride layer, or hexagonal boron nitride which is a two-dimensional insulating material.

The sensing electrode 40 may be extended in the first direction on the interlayer insulating layer 30. The sensing electrode 40 in the first direction may include a channel 42, a first terminal 44, and a second terminal 46. The channel 42 may be disposed between the heaters 50. The first terminal 44 and the second terminal 46 may be connected to both sides of the channel 42. The sensing electrode 40 may include the graphene or graphene oxide (GO). Through the bonding of the defect portions at the surface of the graphene or the GO with molecules for detection, a $sp^2$ bonding structure may be transformed into a $sp^3$ bonding structure. In this case, the conductivity of the sensing electrode 40 may be changed. In addition, the graphene or the GO may be transparent.

The heaters 50 may be disposed in the second direction crossing the first direction, at both sides of the sensing electrode 40. The heaters 50 may include transparent graphene. Thus, the gas sensor according to the first embodiment of the inventive concept may be transparent and flexible.

Materials to be sensed of a gas phase may be combined with the channel 42 of the sensing electrode 40 and may generate the change of the electric conductivity of the channel 42. A control part (not illustrated) may judge the concentration or the amount of the materials to be sensed in the atmosphere from the change of the electric conductivity of the channel 42. In this case, the materials to be sensed may be accumulated and stacked on the surface of the channel 42 with the lapse of time. The lower heater layer 20 and the heaters 50 may heat the interlayer insulating layer 30, the sensing electrode 40, and the materials to be sensed. The materials to be sensed may be evaporated by the heat from the lower heater layer 20 and the heaters 50.

Figure 4:
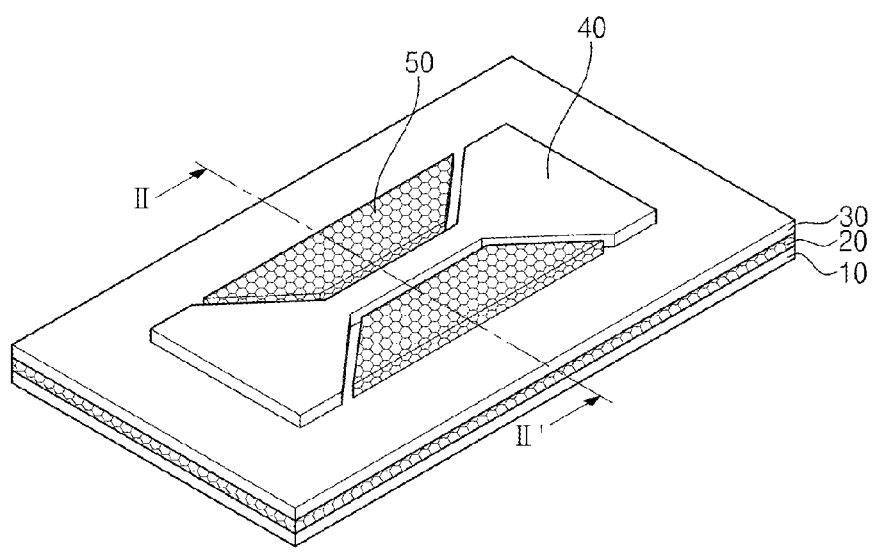
FIG. 4 is a perspective view of a gas sensor according to the first application embodiment of the inventive concept.
Figure 5:
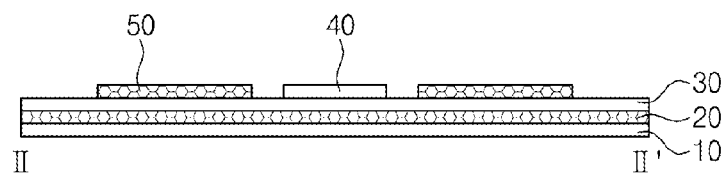
FIG. 5 is a cross-sectional view taken along line II-II' of FIG. 4.
Figure 6:
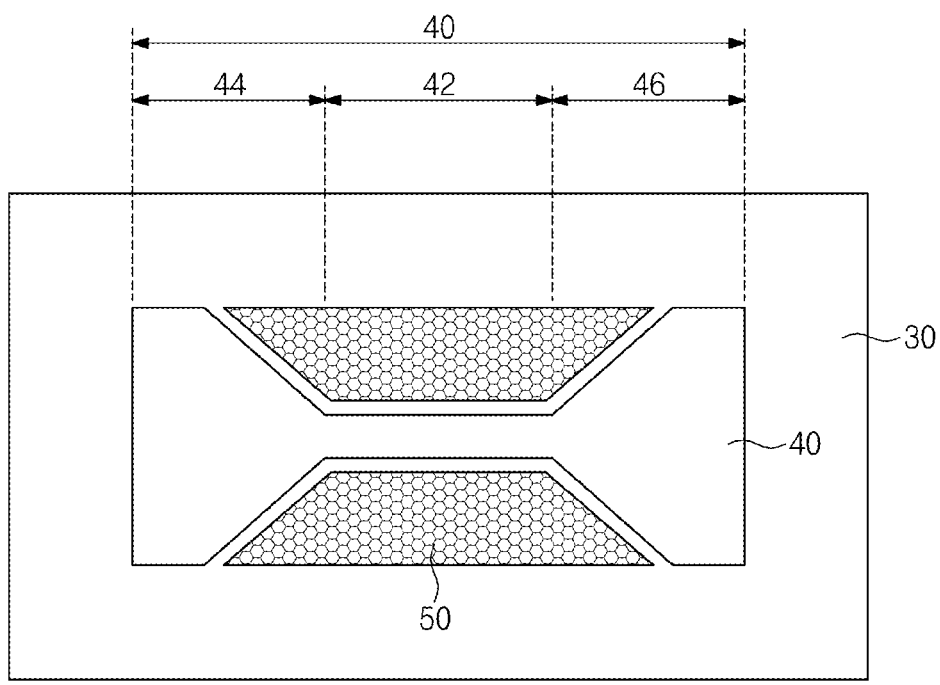
FIG. 6 is a plan view of FIG. 4.

FIG. 4 is a perspective view of a gas sensor according to the first application embodiment of the inventive concept. FIG. 5 is a cross-sectional view taken along line II-II' of FIG. 4. FIG. 6 is a plan view of FIG. 4.

Referring to FIGS. 4 to 6, the gas sensor according to the first application embodiment of the inventive concept may include a sensing electrode 40 including transition metal dichalcogenides (TMDCs). In the first application embodiment, the graphene or the GO of the sensing electrode 40 in the first embodiment is replaced with the TMDCs. The TMDCs may include molybdenum disulfide ($MoS_2$), tungsten disulfide ($WS_2$), or niobium diselenide ($NbSe_2$). Similarly, the change of the conductivity may be generated through the functionalization between molecules of the TMDCs and the materials to be sensed. A channel 42 may have a line width of from about 10 nm to about 1 μm. When the TMDCs is used as the channel 42 having minute line width, the channel 42 may be transparent. Thus, the gas sensor according to the first application embodiment may be transparent.

Figure 7:
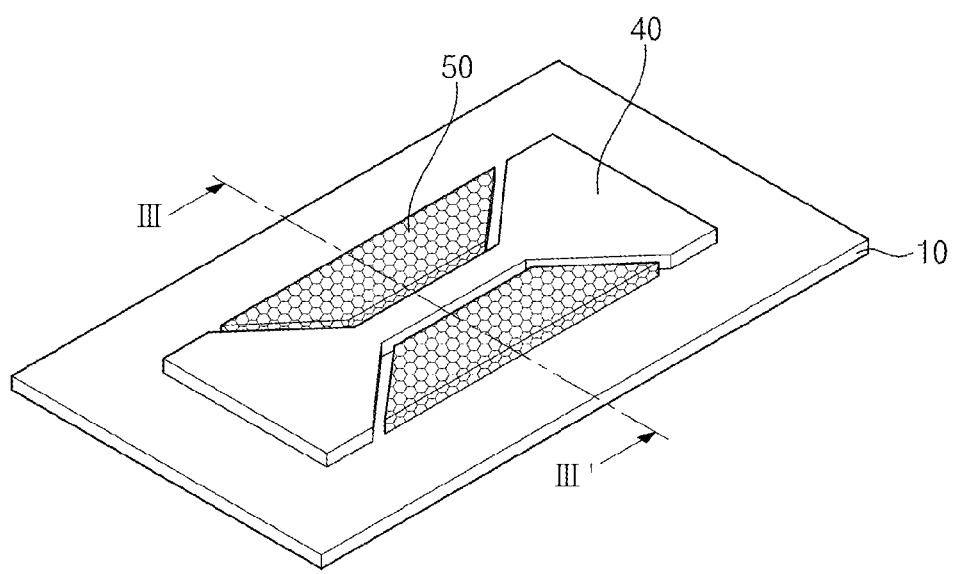
FIG. 7 is a perspective view of a gas sensor according to the second application embodiment of the inventive concept.
Figure 8:
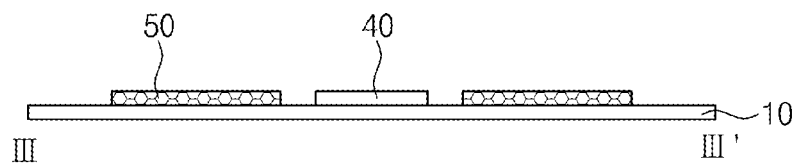
FIG. 8 is a cross-sectional view taken along line III-III' of FIG. 7.
Figure 9:
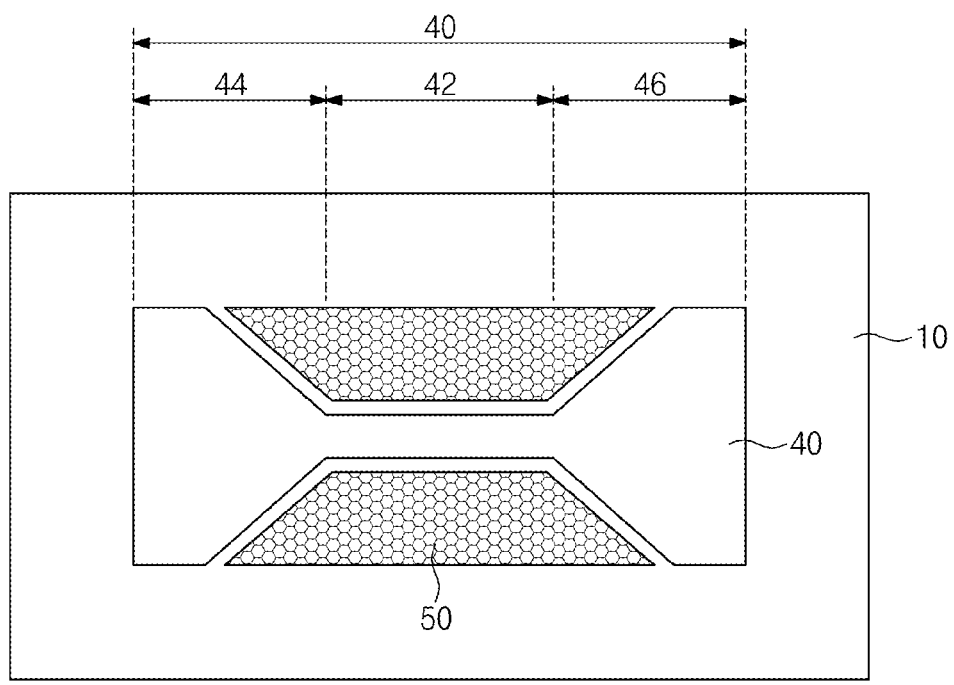
FIG. 9 is a plan view of FIG. 7.

FIG. 7 is a perspective view of a gas sensor according to the second application embodiment of the inventive concept. FIG. 8 is a cross-sectional view taken along line III-III' of FIG. 7. FIG. 9 is a plan view of FIG. 7.

Referring to FIGS. 7 to 9, a gas sensor according to the second application embodiment of the inventive concept may include heaters 50 disposed at both sides of a sensing electrode 40 including the TMDCs. In the second application embodiment, the graphene or the GO of the sensing electrode 40 is replaced with the TMDCs, and the lower heater layer 20 is omitted from the first embodiment. In the second application embodiment, the lower heater layer 20 is omitted from the first application embodiment. The heaters 50 may heat the sensing electrode 40. The materials to be sensed generated on the sensing electrode 40 may be evaporated by the heat from the heaters 50.

Hereinafter, the manufacturing method of the gas sensors according to the first embodiment, the first application embodiment, and the second application embodiment of the inventive concept will be described.

Figure 10:
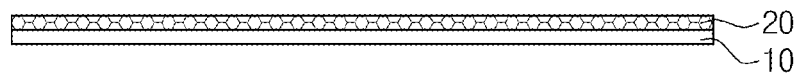
FIGS. 10 and 11 are cross-sectional views illustrating the processes of a manufacturing method of the gas sensor according to the first embodiment of the inventive concept based on FIG. 2.
Figure 11:
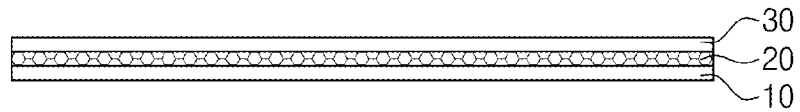

FIGS. 10 and 11 are cross-sectional views illustrating the processes of the manufacturing method of the gas sensor according to the first embodiment of the inventive concept based on FIG. 2.

Referring to FIG. 10, the lower heater layer 20 is formed on the substrate 10. The lower heater layer 20 may include graphene formed by means of a chemical vapor deposition method.

Referring to FIG. 11, the interlayer insulating layer 30 is formed on the lower heater layer 30. The interlayer insulating layer 30 may include a silicon oxide layer, a silicon nitride layer, or a hexagonal boron nitride layer, formed by the chemical vapor deposition method.

Referring to FIG. 2, the sensing electrode 40 and the heaters 50 may be formed on the interlayer insulating layer 30. The sensing electrode 40 and the heaters 50 may be formed simultaneously through the deposition process of the graphene and the patterning process of the graphene. The deposition process may include a chemical vapor deposition process. The patterning process may include a photolithography process and an etching process of the graphene. According to the manufacturing method of the gas sensor according to an embodiment of the inventive concept, the productivity may be improved.

Figure 12:
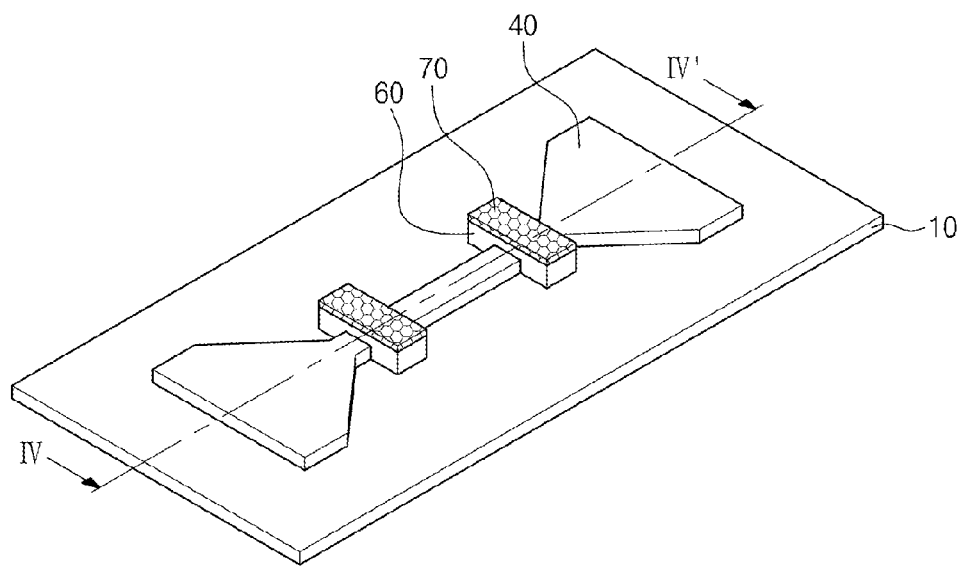
FIG. 12 is a perspective view of a gas sensor according to the second embodiment of the inventive concept.
Figure 13:
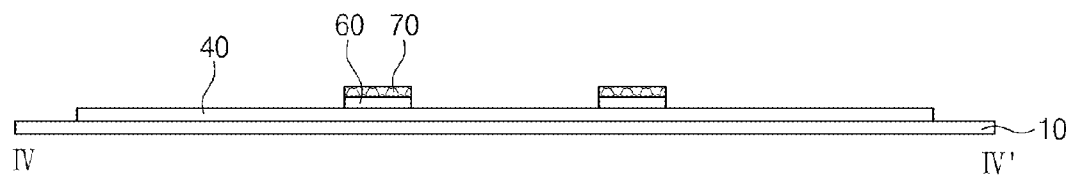
FIG. 13 is a cross-sectional view taken along line IV-IV' of FIG. 12.
Figure 14:
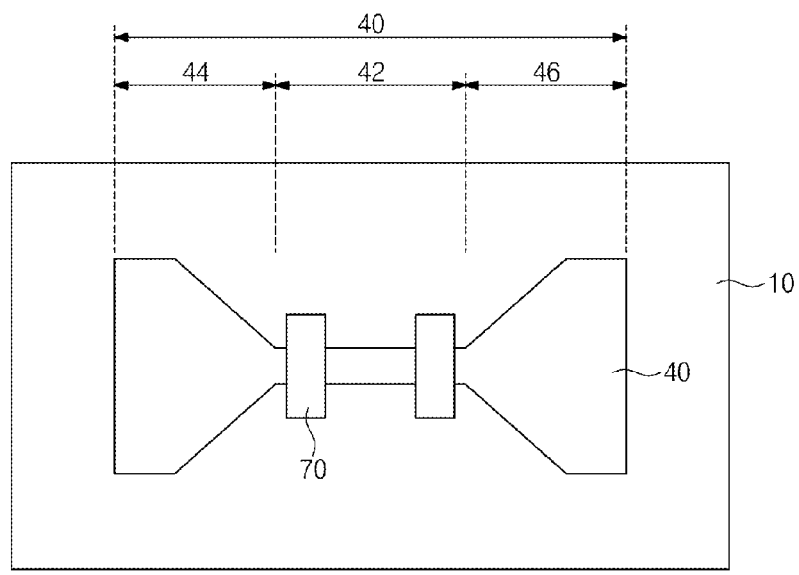
FIG. 14 is a plan view of FIG. 12.

FIG. 12 is a perspective view of a gas sensor according to the second embodiment of the inventive concept. FIG. 13 is a cross-sectional view taken along line IV-IV' of FIG. 13. FIG. 14 is a plan view of FIG. 12.

Referring to FIGS. 12 to 14, the gas sensor according to the second embodiment of the inventive concept may include a plurality of upper insulating patterns 60 disposed in crossing direction of the sensing electrode 40, and upper heaters 70. The upper insulating patterns 60 and the upper heaters 70 may be disposed on the sensing electrode 40. The upper insulating patterns 60 may be separately disposed at both end portions of the sensing electrode 40. According to an embodiment of the inventive concept, the upper insulating patterns 60 and the upper heaters 70 may be disposed on the channel 42 of the sensing electrode 40. The upper heaters may be disposed on the upper insulating patterns 60. The upper insulating patterns 60 may insulate the upper heaters 70 and the sensing electrode 40. For example, the upper insulating patterns 60 may include a hexagonal boron nitride layer. The heaters 70 may include the graphene. The graphene and the hexagonal boron nitride layer may have the light absorbance of about 2% or less. In addition, the graphene and the hexagonal boron nitride layer may be bent to the same direction as the substrate 10.

Therefore, the gas sensor according to the second embodiment of the inventive concept may be transparent and flexible. However, the present invention is not limited thereto, and various modifications may be made. For example, the plurality of heaters 50 and the lower heater layer 20 under the sensing electrode 40 in the first embodiment, may be further disposed under the upper heaters 70 at both sides of the sensing electrode 40.

Hereinafter, the manufacturing method of the gas sensor including the above-described constitution according to the second embodiment of the inventive concept will be described.

Figure 15:
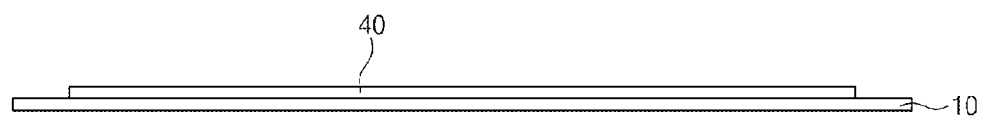
FIGS. 15 to 17 are cross-sectional views illustrating the processes of a manufacturing method of the gas sensor according to the second embodiment of the inventive concept based on FIG. 13.
Figure 16:
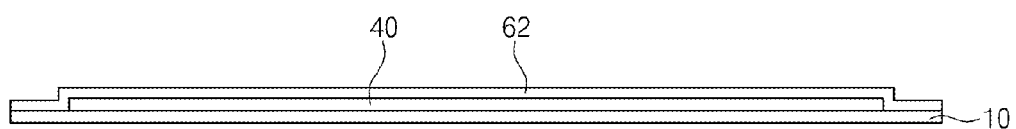
Figure 17:
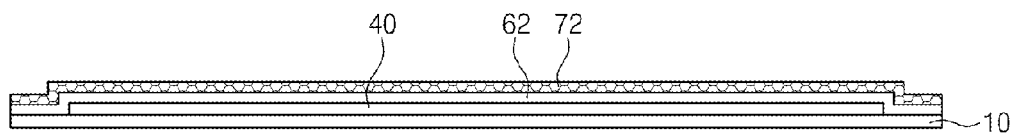

FIGS. 15 to 17 are cross-sectional views illustrating the processes of the manufacturing method of the gas sensor according to the second embodiment of the inventive concept based on FIG. 13.

Referring to FIG. 15, the sensing electrode 40 may be formed on the substrate 10. The sensing electrode 40 may be formed through the deposition process of TMDCs, a photolithography process, and an etching process. The deposition process may include a chemical vapor deposition process. However, the present invention is not limited thereto, and various modifications may be made. As in FIGS. 10 and 11, the lower heater layer 20 may be formed between the substrate 10 and the sensing electrode 40, and a plurality of heaters 50 may be formed at both sides of the sensing electrode 40.

Referring to FIG. 16, an upper insulating layer 62 is formed on the sensing electrode 40 and the substrate 10. The upper insulating layer 62 may include the hexagonal boron nitride layer formed by means of a chemical vapor deposition method.

Referring to FIG. 17, an upper heater layer 72 is formed on the upper insulating layer 62. The upper heater layer 72 may include the graphene formed by means of a mechanical method or a chemical vapor deposition method.

Referring to FIG. 13, the upper heater layer 72 and the upper insulating layer 62 are patterned, and the upper heaters 70 and the upper insulating patterns 60 are formed. The upper heater layer 72 and the upper insulating layer 62 may be patterned by conducting a photolithography process and an etching process.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:
1. A manufacturing method of a gas sensor, the method comprising:
forming a substrate;
forming a sensing electrode in a first direction on the substrate; and forming a plurality of heaters on the substrate in a second direction crossing the first direction at both sides of the sensing electrode, wherein:

the sensing electrode is combined with materials to be sensed of a gas;

the plurality of heaters are electrically insulated from the sensing electrode; and the plurality of heaters comprise graphene.

2. The manufacturing method of claim 1, further comprising:

forming a lower heater layer between the sensing electrode and the substrate; and forming an interlayer insulating layer between the lower heater layer and the sensing electrode, wherein the lower heater layer is electrically insulated from the sensing electrode.

3. A manufacturing method of a gas sensor, the method comprising:

forming a substrate;

forming a sensing electrode on the substrate;

forming an upper insulating layer on the sensing electrode and the substrate;

forming an upper heater layer on the upper insulating layer; and patterning the upper heater layer and the upper insulating layer to form upper insulating patterns and upper heaters at both side end portions of the sensing electrode, wherein:

the substrate, the sensing electrode, the upper insulating patterns and the upper heaters are stacked in this order;

the sensing electrode is combined with materials to be sensed of a gas;

the upper heaters are electrically insulated from the sensing electrode; and the upper heaters comprise graphene.

4. The manufacturing method of claim 2, wherein the lower heater layer comprises graphene.

5. The manufacturing method of claim 2, wherein the interlayer insulating layer comprises a transparent dielectric material.

6. The manufacturing method of claim 3, wherein the upper insulating patterns comprise a transparent dielectric material.

7. The manufacturing method of claim 1, wherein the substrate includes a transparent flexible substrate.

8. The manufacturing method of claim 1, wherein the sensing electrode comprises graphene.

9. The manufacturing method of claim 3, wherein:

the sensing electrode includes a first terminal, a second terminal and a channel connecting the first and second terminals, the channel extending from the first terminal to the second terminal in a first direction;

each of the upper insulating patterns, taken from a plan view, crosses the channel in a second direction, each of the upper insulating patterns having a lower surface facing the substrate and an upper surface opposite to the lower surface; and each of the upper heaters is disposed on a corresponding one of the upper insulating patterns to cover the entire upper surface of the corresponding one of the upper insulating patterns without extending beyond the upper surface of the corresponding one of the upper insulating patterns.

10. The manufacturing method of claim 1, wherein the sensing electrode includes a first terminal, a second terminal and a channel that connects the first and second terminals and is disposed between the heaters, wherein the channel and the plurality of heaters are disposed along the second direction.

11. The manufacturing method of claim 1, wherein the plurality of heaters, taken from the plan view, is spaced apart from the sensing electrode.

12. The manufacturing method of claim 1, wherein the sensing electrode is formed of a single layer of carbon atoms, the single layer having a thickness same as that of a single carbon atom.

13. The manufacturing method of claim 3, wherein the upper heaters are formed of a single layer of carbon atoms, the single layer having a thickness same as that of a single carbon atom.

14. The manufacturing method of claim 1, wherein the sensing electrode and the plurality of heaters are formed at the same level.

15. The manufacturing method of claim 2, wherein the lower heater layer covers an entire upper surface of the substrate.

16. The manufacturing method of claim 2, wherein a lower surface of the sensing electrode and lower surfaces of the plurality of heaters are disposed at the same level and come in direct contact with an upper surface of the interlayer insulating layer.

17. The manufacturing method of claim 1, wherein:

the sensing electrode includes a first terminal, a second terminal and a channel that extends in the first direction from the first terminal to the second terminal;

the channel has a width narrower than a width of the first terminal and a width of the second terminal, the width of the channel being a distance between two opposite sides of the channel including a first side and a second side;

the plurality of heaters include a first heater and a second heater;

the first heater, taken from the plan view, is disposed in an area surrounded by the first terminal, the first side of the channel and the second terminal, and faces the first side of the channel with a gap; and the second heater, taken from the plan view, is disposed in an area surrounded by the first terminal, the second side of the channel and the second terminal, and faces the second side of the channel with a gap.

18. The manufacturing method of claim 3, wherein:

the sensing electrode includes a first terminal, a second terminal and a channel connecting the first and second terminals, the channel extending from the first terminal to the second terminal in a first direction, the channel having a width narrower than a width of the first terminal and a width of the second terminal; and the first and second terminals of the sensing electrode are exposed without being covered by the upper insulating patterns.

19. The manufacturing method of claim 8, wherein the sensing electrode and the plurality of heaters are formed simultaneously through depositing and patterning the graphene.

20. The manufacturing method of claim 3, wherein the sensing electrode comprises transition metal dichalcogenides.

* * * * *